US006204057B1

(12) United States Patent
Schnetter et al.

(10) Patent No.: US 6,204,057 B1
(45) Date of Patent: Mar. 20, 2001

(54) POLYNUCLEOTIDES AND THE PROTEINS ENCODED THEREBY, SUITABLE FOR CONTROLLING LAMELLICORN BEETLES

(75) Inventors: Wolfgang Schnetter, Bammental; Lutz Krieger; Jiambing Zhang, both of Heidelberg, all of (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/408,820

(22) Filed: Sep. 29, 1999

Related U.S. Application Data

(63) Continuation of application No. 09/051,454, filed as application No. PCT/DE96/01979 on Oct. 17, 1996, now abandoned.

(30) Foreign Application Priority Data

Oct. 18, 1995 (DE) .............................................. 195 40 223

(51) Int. Cl.$^7$ ............................ A01H 1/00; C07H 21/04; C07K 14/32; C12N 5/14

(52) U.S. Cl. ........................ 435/418; 435/69.1; 435/70.1; 435/71.1; 435/71.2; 435/71.3; 435/410; 435/419; 435/243; 435/252.5; 435/252.8; 435/320.1; 530/825; 530/350; 536/23.7; 536/23.71; 536/24.1; 536/23.1; 800/278; 800/279; 800/288; 800/298; 800/301; 800/302

(58) Field of Search ................................ 435/69.1, 70.1, 435/71.1, 71.2, 71.3, 410, 418, 419, 243, 252.5, 252.8, 320.1; 530/825, 350; 536/23.7, 23.71, 24.1, 23.1; 800/278, 279, 288, 298, 301, 302

(56) References Cited

FOREIGN PATENT DOCUMENTS

WO87/05928 10/1987 (WO) .

WO93/15206 8/1993 (WO) .

OTHER PUBLICATIONS

Wu et al. FEMS Microbiology Letters. 1991 vol. 81, p. 31–36.*

Hurpin et al., Comparison of Activity of Certain pathogens of the Cockchafer *Melolontha melolontha* in Plots of Natural Meadowland, Journal of invertebrate Pathology, 19: 291–298 (1972).

Zhang et al., Cloning and Analysis of the First Cry Gene from *Bacillus popilliae*, Journal of Bacteriology, 179(13): 4336–4341, Jul. 1997.

Zhang et al., Characterization of a Novel Cry Gene from *Bacillus popillae* and implications for its toxicology, Jul. 12, 1996 EMBL Database Entry BPCRYBP1;Accesson No. X99049.

McDonald et al., Applied and Environmental Microbiology, vol. 61:No.6, 2446–2449 (1995).

Dingman, J. Bacteriol., vol. 172:No.10, 6156–6159 (1990).

Weiner, Can. J. Microbiol. vol. 24: 1557–1561 (1978).

* cited by examiner

*Primary Examiner*—Phuong T. Bui
(74) *Attorney, Agent, or Firm*—J. Timothy Meigs

(57) ABSTRACT

The invention relates to isolated polynucleotides and the proteins encoded thereby, and to their use in controlling lamellicorn beetles (Scarabaeidae). In addition, the invention relates to a method of producing those proteins. The polynucleotides of the invention encode proteins that are identical to or at least related to the crystal proteins characteristic of *Bacillus popilliae* and that are suitable for the inhibition of the feeding activity and/or for the destruction of adult and/or larval scarabaeids, especially Melolontha species and species closely related thereto.

17 Claims, No Drawings

SEQUENCE LISTING

<160> NUMBER OF SEQ ID NOS: 2

<210> SEQ ID NO 1
<211> LENGTH: 2121
<212> TYPE: DNA
<213> ORGANISM: Bacillus popilliae
<220> FEATURE:
<223> OTHER INFORMATION: strain subspecies: melolonthae H1; stage of develpment: vegetative phase; cell type: vegetative cell
<220> FEATURE:
<223> OTHER INFORMATION: immediate origin: isolate from the haemolymph of Mololontha melolontha individuals captured on open land
<220> FEATURE:
<221> NAME/KEY: misc_feature
<222> LOCATION: (1)..(2118)
<223> OTHER INFORMATION: coding sequence for crystal protein determined by experiment and by similarity to the cry2 gene region from Bacillus thuringiensis

<400> SEQUENCE: 1

```
atgaacaata attttaatgg tggaaataat acaggaaata actttactgg aaatactcta     60
agcaacggaa tttgtacgaa aaaaaatatg aaaggaaccc taagcagaac tgctatattt    120
tcagatggga ttagtgatga tttaatttgt tgtctagatc ctatatataa caataacgat    180
aacaataacg atgctatttg tgatgagtta ggtttaactc caatagataa caatacgata    240
tgcagtactg attttactcc cataaatgta atgagaacag atccttttcg caagaaatca    300
acacaagaac tcacaaggga atggacagaa tggaaagaaa atagtccttc tttgtttaca    360
ccggcaattg taggtgtcgt taccagtttt cttcttcaat cattaaaaaa acaagcaact    420
agctttcttt taaaaacttt gacagaccta atatttccta ataacagttc gttaacgatg    480
gaagagattt tacgagccac ggaacaatat gttcaggaac ggcttgatac tgataccgcg    540
aatcgtgtgt cacaggaact agtaggtttg aagaataacc taacaacctt taacgatcaa    600
gtcgaagatt ttttacaaaa tagagttggg atttcaccac ttgcaattat agattcgatt    660
aataccatgc aacaactttt tgttaataga ttgccacagt tccaagtaag tggctatcaa    720
gtattattat tacctttatt tgctcaagca gccacgcttc atttaacttt tttacgagat    780
gttatcatta atgccgatga atggaatata ccgacagctc aattgaacac gtatacgcga    840
tattttaaag aatatatagc ggaatattcc aattatgctt tatccaccta tgatgatgga    900
tttagaacaa gattttatcc aagaaatact ttagaagaca tgttacaatt caaaacattt    960
atgacattaa atgcactaga tcttgtttca atttggtcgt tgctaaaata tgtaaaccta   1020
tatgtaagca ctagtgcaaa tttatataat ataggggata ataaggtgaa tgagggagca   1080
tatccaatct cctatggccc gttctttaac tcctatattc agacgaaatc gaattatgta   1140
ttatccggtg tatcagggat tggcgctcgc tttacttata gtactgtctt aggacgatac   1200
cttcatgatg accttaaaaa tattatcacc acttatgtag gtgggactca aggaccaaac   1260
attggcgttc agctttctac aaccgaactc gatgaactaa aaaaacaaca acaagctact   1320
agagattcat tagtagactt tcaatttttc acattgaatt gtatgctacc aaatccgatt   1380
actgcacctt atttcgctac cagcttatat gaatctcgtt attcatcaat tggtggatac   1440
cttcgtaagg acgtctttaa aagtgaagat agtacctgcg gtcttggtaa cccgggtgct   1500
tggacatctt atccagatta ttatattacg aatatttctg caactgtaca aataaacgga   1560
gaaaatacag atacaacacc gttatatttc aaagaaaaca gacccataac ttctactagg   1620
```

-continued

```
ggtgtaaata aagttatcgc tgtttataat aggaaagcca atatagcagg tacaaatcaa    1680
aatggtacca tgatacatca agcacctcct gatggtaccg gttttactgt atctccattg    1740
catccgagcg ctaatacaat tacttcttat attaaagaga attatggaaa tagtggtgat    1800
tcactccacc tgaagggtca aggctatcta cattacatgc tttcagggaa tgggcaggat    1860
cgctacagat tagttttgag gttatctgga gctgcaaatc agataaaact tcagtctccg    1920
actactagta tatacgcttt cgatacatct actaataacg aaggaattac agacaatggt    1980
tcaaaattta aagatttcgc attttcaacc ccttttgtta tacctgaaca aaaagaaata    2040
gttttatatt tcgagggtgt aggatccctt gatctaatga atcttatctt tcttccagca    2100
gatgacactc ctctttatta g                                              2121
```

<210> SEQ ID NO 2
<211> LENGTH: 706
<212> TYPE: PRT
<213> ORGANISM: Bacillus popilliae
<220> FEATURE:
<223> OTHER INFORMATION: strain subspecies: melolonthae H1; stage of development: spore stage; cell type: sporangium
<220> FEATURE:
<223> OTHER INFORMATION: immediate origin: isolate from the haemolymph of Melolontha melolontha individuals captured on open ground
<220> FEATURE:
<221> NAME/KEY: PEPTIDE
<222> LOCATION: (1)..(706)
<223> OTHER INFORMATION: mature protein crystal peptide determined by experiment

<400> SEQUENCE: 2

```
Met Asn Asn Asn Phe Asn Gly Gly Asn Thr Gly Asn Asn Phe Thr
 1               5                  10                  15

Gly Asn Thr Leu Ser Asn Gly Ile Cys Thr Lys Lys Asn Met Lys Gly
             20                  25                  30

Thr Leu Ser Arg Thr Ala Ile Phe Ser Asp Gly Ile Ser Asp Asp Leu
         35                  40                  45

Ile Cys Cys Leu Asp Pro Ile Tyr Asn Asn Asp Asn Asn Asn Asp
     50                  55                  60

Ala Ile Cys Asp Glu Leu Gly Leu Thr Pro Ile Asp Asn Asn Thr Ile
 65                  70                  75                  80

Cys Ser Thr Asp Phe Thr Pro Ile Asn Val Met Arg Thr Asp Pro Phe
                 85                  90                  95

Arg Lys Lys Ser Thr Gln Glu Leu Thr Arg Glu Trp Thr Glu Trp Lys
            100                 105                 110

Glu Asn Ser Pro Ser Leu Phe Thr Pro Ala Ile Val Gly Val Val Thr
        115                 120                 125

Ser Phe Leu Leu Gln Ser Leu Lys Lys Gln Ala Thr Ser Phe Leu Leu
    130                 135                 140

Lys Thr Leu Thr Asp Leu Leu Phe Pro Asn Asn Ser Ser Leu Thr Met
145                 150                 155                 160

Glu Glu Ile Leu Arg Ala Thr Glu Gln Tyr Val Gln Glu Arg Leu Asp
                165                 170                 175

Thr Asp Thr Ala Asn Arg Val Ser Gln Glu Leu Val Gly Leu Lys Asn
            180                 185                 190

Asn Leu Thr Thr Phe Asn Asp Gln Val Glu Asp Phe Leu Gln Asn Arg
        195                 200                 205

Val Gly Ile Ser Pro Leu Ala Ile Ile Asp Ser Ile Asn Thr Met Gln
    210                 215                 220
```

```
Gln Leu Phe Val Asn Arg Leu Pro Gln Phe Gln Val Ser Gly Tyr Gln
225                 230                 235                 240

Val Leu Leu Leu Pro Leu Phe Ala Gln Ala Ala Thr Leu His Leu Thr
            245                 250                 255

Phe Leu Arg Asp Val Ile Ile Asn Ala Asp Glu Trp Asn Ile Pro Thr
            260                 265                 270

Ala Gln Leu Asn Thr Tyr Thr Arg Tyr Phe Lys Glu Tyr Ile Ala Glu
            275                 280                 285

Tyr Ser Asn Tyr Ala Leu Ser Thr Tyr Asp Asp Gly Phe Arg Thr Arg
290                 295                 300

Phe Tyr Pro Arg Asn Thr Leu Glu Asp Met Leu Gln Phe Lys Thr Phe
305                 310                 315                 320

Met Thr Leu Asn Ala Leu Asp Leu Val Ser Ile Trp Ser Leu Leu Lys
            325                 330                 335

Tyr Val Asn Leu Tyr Val Ser Thr Ser Ala Asn Leu Tyr Asn Ile Gly
            340                 345                 350

Asp Asn Lys Val Asn Glu Gly Ala Tyr Pro Ile Ser Tyr Gly Pro Phe
            355                 360                 365

Phe Asn Ser Tyr Ile Gln Thr Lys Ser Asn Tyr Val Leu Ser Gly Val
370                 375                 380

Ser Gly Ile Gly Ala Arg Phe Thr Tyr Ser Thr Val Leu Gly Arg Tyr
385                 390                 395                 400

Leu His Asp Asp Leu Lys Asn Ile Ile Thr Thr Tyr Val Gly Gly Thr
            405                 410                 415

Gln Gly Pro Asn Ile Gly Val Gln Leu Ser Thr Thr Glu Leu Asp Glu
            420                 425                 430

Leu Lys Lys Gln Gln Gln Ala Thr Arg Asp Ser Leu Val Asp Phe Gln
            435                 440                 445

Phe Phe Thr Leu Asn Cys Met Leu Pro Asn Pro Ile Thr Ala Pro Tyr
            450                 455                 460

Phe Ala Thr Ser Leu Tyr Glu Ser Arg Tyr Ser Ser Ile Gly Gly Tyr
465                 470                 475                 480

Leu Arg Lys Asp Val Phe Lys Ser Glu Asp Ser Thr Cys Gly Leu Gly
            485                 490                 495

Asn Pro Gly Ala Trp Thr Ser Tyr Pro Asp Tyr Ile Thr Asn Ile
            500                 505                 510

Ser Ala Thr Val Gln Ile Asn Gly Glu Asn Thr Asp Thr Thr Pro Leu
            515                 520                 525

Tyr Phe Lys Glu Asn Arg Pro Ile Thr Ser Thr Arg Gly Val Asn Lys
530                 535                 540

Val Ile Ala Val Tyr Asn Arg Lys Ala Asn Ile Ala Gly Thr Asn Gln
545                 550                 555                 560

Asn Gly Thr Met Ile His Gln Ala Pro Pro Asp Gly Thr Gly Phe Thr
            565                 570                 575

Val Ser Pro Leu His Pro Ser Ala Asn Thr Ile Thr Ser Tyr Ile Lys
            580                 585                 590

Glu Asn Tyr Gly Asn Ser Gly Asp Ser Leu His Leu Lys Gly Gln Gly
            595                 600                 605

Tyr Leu His Tyr Met Leu Ser Gly Asn Gly Gln Asp Arg Tyr Arg Leu
            610                 615                 620

Val Leu Arg Leu Ser Gly Ala Ala Asn Gln Ile Lys Leu Gln Ser Pro
625                 630                 635                 640

Thr Thr Ser Ile Tyr Ala Phe Asp Thr Ser Thr Asn Asn Glu Gly Ile
```

```
                         645                 650                 655
Thr Asp Asn Gly Ser Lys Phe Lys Asp Phe Ala Phe Ser Thr Pro Phe
                660                 665                 670
Val Ile Pro Glu Gln Lys Glu Ile Val Leu Tyr Phe Glu Gly Val Gly
            675                 680                 685
Ser Leu Asp Leu Met Asn Leu Ile Phe Leu Pro Ala Asp Asp Thr Pro
        690                 695                 700
Leu Tyr
705
```

POLYNUCLEOTIDES AND THE PROTEINS ENCODED THEREBY, SUITABLE FOR CONTROLLING LAMELLICORN BEETLES

This is a continuation-in-part of U.S. patent application Ser. No. 09/051,454, filed Apr. 7, 1998, now abandoned, which is a §371 of PCT/DE96/01979, filed Oct. 17, 1996, and published Apr. 24, 1997, as WO 97/14798, which claims priority of DE 195 40 223.5, filed Oct. 18,1995. Each of the above applications is hereby incorporated by reference in its entirety into the instant disclosure.

FIELD OF THE INVENTION

The invention relates to isolated polynucleotides and the proteins encoded thereby and to their use in controlling lamellicorn beetles (Scarabaeidae). In addition, the invention relates to a method of producing those proteins.

BACKGROUND OF THE INVENTION

Lamellicorn beetles, such as the cockchafer (*Melolontha melolontha*) and the wood chafer (*Melolontha hippocastani*), and especially their larvae (grubs) can cause serious damage to crops in agriculture and forestry. Since their control by means of chemical insecticides is difficult and environmentally harmful, attempts are increasingly being made to control the reproduction and spread of those insects using biological means. For example, EP 633 936 A1 describes a method in which vegetative cells, spores or protein crystals of certain strains of *Bacillus thuringiensis* are used to control lamellicorn beetles. The effectiveness of that method is not satisfactory, however.

WO 87 05928 proposes the use of *Bacillus popilliae* (*B. popilliae*) spores in the biological control of scarabaeid larvae.

*B. popilliae* is the causative organism of so-called milky disease in larvae of may bugs and other lamellicorn beetles. The larvae infested with the bacillus have high concentrations of vegetative cells and sporangia of *B. popilliae* in their haemolymph, which result in a milky-white discolouration of the grub.

*B. popilliae* was first described by Dutky as a cause of milky disease in the Japanese beetle (*Popillia japonica*) in the U.S.A. (in: *Journal of Agriculftural Research* 61 (1940) pages 57–68, "Two new sporeforming bacteria causing milky disease of the Japanese beetle") and was later identified by Hurpin and Vago and by Wille also in grubs of the cockchafer (*Melolontha melolontha*) (B. Hurpin and C. Vago in: *Entomophaga* 3 (1958) pages 285–330, "Les maladies du hanneton commun (*Melolontha melolontha* L. (Col., Scarabaeidae)"; H. Wille in: *Mitteilungen. Schweizerische Entomologische Gesellschaft* 29 (1956) pages 271–282: "*Bacillus fribourgensis* n. sp., Erreger einer "milky disease" im Engerling von *Melolontha melolontha* L.").

Characteristics of the *B. popilliae* bacterium are inter alia that it does not form catalase and that most isolates are resistant to the antibiotic vancomycin and during sporulation form a distinctive protein crystal which is arranged inside the spindle-shaped sporangium next to the actual spore.

In its capacity as a pathogen for scarabaeids, *B. popilliae* has a high degree of specificity. The *B. popilliae* subspecies isolated from different species of scarabaeids differ in some cases considerably in their growth characteristics, in the composition of the protein crystal and in their plasmids.

The infestation of beetle larvae with *B. popilliae* is effected by peroral ingestion of the sporangia. The spores germinate in the gut of the larvae and the vegetative bacterial cells penetrate through the gut epithelium and the basal membrane into the haemolymph where they multiply during the subsequent three to four weeks. The *B. popilliae* cells then sporulate, which ultimately leads to the death of the beetle larva.

In contrast to other Bacillus species, however, under in vitro conditions *B. popilliae* forms predominantly vegetative cells and forms spores only exceptionally. Although WO 87 05 928 describes a method of obtaining the spores in vitro, in which the vegetative cells of *B. popilliae* are cultured in a defined medium and are finally stimulated to sporulate by the addition of a specific adjuvant, that method achieves a sporulation rate of only about 80%. In order to obtain quantities of infectious spore material sufficient for biological control it is therefore necessary to invest considerable resources in terms of equipment, personnel and financial expenditure, which make that method economically unviable and therefore unsuitable for practical purposes.

The aim of the present invention is therefore to provide biological means for controlling scarabaeids that enable those pests to be controlled satisfactorily and that are technically simple and economical to produce also on a large scale. Furthermore, means whose application minimizes the burden on the environment are desirable.

SUMMARY OF THE INVENTION

The present invention addresses the aforementioned needs by providing novel polynucleotide sequences isolated from *B. popilliae*. The proteins encoded by the novel polynucleotide sequences are active against lamellicorn beetles (Scarabaeidae) and can be used in multiple insect control strategies, resulting in maximal efficiency with minimal impact on the environment.

Hence, in one embodiment, the present invention is directed to an isolated nucleic acid molecule comprising a nucleotide sequence that encodes a *B. popilliae* crystal protein. In another embodiment, the present invention is directed to an isolated nucleic acid molecule comprising a nucleotide sequence that encodes a *B. popilliae* crystal protein that comprises the amino acid sequence set forth in SEQ ID NO:2. In a particularly preferred embodiment, the present invention is directed to an isolated nucleic acid molecule comprising a nucleotide sequence that encodes a *B. popilliae* crystal protein, wherein the nucleotide sequence is SEQ ID NO:1.

The present invention is also directed to an isolated nucleic acid molecule comprising a nucleotide sequence that encodes an insecticidal protein comprising an amino acid sequence that is the translation product of a nucleic acid sequence whose complement hybridizes to SEQ ID NO:1 under hybridization conditions of 7% sodium dodecyl sulfate (SDS), 0.5 M NaPO$_4$, 1 mM EDTA at 50° C. with washing in 0.1×SSC, 0.1% SDS at 50° C., or under hybridization conditions of 7% sodium dodecyl sulfate (SDS), 0.5 M NaPO$_4$, 1 mM EDTA at 50° C. with washing in 0.1×SSC, 0.1% SDS at 65° C.

The present invention is further directed to an isolated nucleic acid molecule comprising a nucleotide sequence that encodes an insecticidal protein, wherein said nucleotide sequence has a complement that hybridizes to a SEQ ID NO:1 under hybridization conditions of 7% sodium dodecyl sulfate (SDS), 0.5 M NaPO$_4$, 1 mM EDTA at 50° C. with washing in 0.1×SSC, 0.1% SDS at 50° C., or under hybridization conditions of 7% sodium dodecyl sulfate (SDS), 0.5 M NaPO$_4$, 1 mM EDTA at 50° C. with washing in 0.1×SSC, 0.1% SDS at 65° C.

The present invention is still further directed to an isolated nucleic acid molecule comprising a nucleotide sequence that encodes an insecticidal protein, wherein said nucleotide sequence comprises a 20, 25, 30, 35, 40, 45, or 50 (preferably 20) base pair nucleotide portion identical in sequence to a respective consecutive 20, 25, 30, 35, 40, 45, or 50 (preferably 20) base pair nucleotide portion of SEQ ID NO:1.

The present invention also provides a chimeric gene comprising a heterologous promoter sequence operatively linked to a nucleic acid molecule of the invention. Further, the present invention provides a recombinant vector comprising such a chimeric gene. Still further, the present invention provides a transgenic host cell comprising such a chimeric gene. A transgenic host cell according to this aspect of the invention may be a transgenic bacterial cell, a transgenic yeast cell, or a transgenic plant cell, preferably a transgenic plant cell. Even further, the present invention provides a transgenic plant comprising such a transgenic plant cell. Preferably, the transgenic plant is one of the following agronomically important crops: maize, rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane. The present invention also provides seed of such a transgenic plant.

In yet another aspect, the present invention provides a *B. popilliae* crystal protein produced by the expression of DNA molecules of the present invention. According to a preferred embodiment, the *B. popilliae* crystal protein of the invention has activity against lamellicorn beetles (Scarabaeidae). According to an especially preferred embodiment, a *B. popilliae* crystal protein of the invention comprises the amino acid sequence set forth in SEQ ID NO:2.

In a further aspect, the present invention provides a method of producing an insect-resistant plant, comprising introducing a nucleic acid molecule of the invention into the plant, wherein the nucleic acid molecule is expressible in the plant in an effective amount to control insects. According to a preferred embodiment, the insects are lamellicom beetles (Scarabaeidae).

In a still further aspect, the present invention provides a method of controlling insects comprising delivering to the insects an effective amount of a *B. popilliae* crystal protein according to the present invention. According to a preferred embodiment, the insects are lamellicorn beetles (Scarabaeidae). Preferably, the *B. popilliae* crystal protein is delivered to the insects orally.

Other aspects and advantages of the present invention will become apparent to those skilled in the art from a study of the following description of the invention and non-limiting examples.

DEFINITIONS

"Activity" of the *B. popilliae* crystal protein of the invention refers to the proteins's function as an orally active insect control agent, especially its ability to disrupt or deter insect feeding, which may or may not cause death of the insect. When a protein of the invention is delivered to the insect, the result is typically death of the insect, or the insect does not feed upon the source that makes the protein available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a protein means that the protein comes in contact with an insect, resulting in toxic effect and control of the insect. The protein can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

A "nucleic acid molecule" or "nucleic acid sequence" is a linear segment of single- or double-stranded DNA or RNA that can be isolated from any source. In the context of the present invention, the nucleic acid molecule is preferably a segment of DNA. "ORF" means open reading frame.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase II and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

BRIEF DESCRIPTION OF THE SEQUENCES IN THE SEQUENCE LISTING

SEQ ID NO:1 is the nucleotide coding sequence of a *Bacillus popilliae* subsp. *melolonthae* H1 crystal protein of the invention.

SEQ ID NO:2 is the amino acid sequence of the *Bacillus popilliae* subsp. *melolonthae* H1 crystal protein of the invention, encoded by SEQ ID NO:1.

DETAILED DESCRIPTION OF THE INVENTION

The present invention provides polynucleotides that encode proteins identical to or at least related to the crystal proteins characteristic of *Bacillus popilliae* and that have all or part of the nucleotide sequence shown in the sequence listing SEQ ID NO:1 or have a nucleotide sequence related thereto and derived therefrom by substitution, deletion, insertion and/or inversion or have a nucleotide sequence that hybridises fully or partly therewith.

It has now surprisingly been established that the protein crystal from *B. popilliae* has a decisive role in the inhibition of feeding in scarabaeid larvae and that that protein crystal results in the death of adult animals after oral administration. The provision of the polynucleotides according to the invention makes it possible for the first time to obtain or to produce those *B. popilliae* protein crystals in virtually unlimited amounts, that is to say especially also on a large biotechnological scale.

The polynucleotides according to the invention themselves can either be obtained from a natural source or produced synthetically or semisynthetically.

They are present especially as a component of a recombinant DNA vector molecule that has the ability to express in a prokaryotic or eukaryotic cell the crystal protein that is characteristic of *Bacillus popilliae* or a protein crystal that is characteristic of *Bacillus popilliae* or a protein that is related thereto. That vector molecule has inter alia the advantage that it can be introduced into any cell, for example of a commercially available, easily cultured bacterial culture of *E. coli* or *Bacillus thuringiensis*, subjected to the control of a promoter already present in the cell or inserted therewith, and both replicated and expressed. Suitable vector molecules are especially plasmids originating from gram-positive bacteria.

To obtain the crystal proteins encoded by the polynucleotides according to the invention by the biotechnology route it is proposed to use transformed host cells comprising a polynucleotide according to the invention that has been linked to a promoter naturally present in the host cell or present therein as a consequence of recombination. The polynucleotide(s) according to the invention is(are) introduced into the host organism, that is to say into a microorganism, a virus, a protozoon, a plant cell or the like, for example by transformation, transduction or conjugation, integrated into the genetic material of those cells or viruses, and expressed.

Host cells that have proved especially suitable are the vegetative cells of *Bacillus thuringiensis*, e.g. *Bacillus thuringiensis* subsp. *kurstaki*. *Bacillus thuringiensis* has been the subject of very thorough investigation and in this system it is comparatively simple to produce the crystal protein of *B. popilliae* also in large amounts.

The protein(s) according to the invention can be used alone or in combination with at least one other substance as a biological insecticide for controlling scarabaeids, that is to say for inhibiting the feeding activity and/or for destroying adult and/or larval scarabaeids, especially Melolontha species and species closely related thereto. The term "substance" here includes chemical and biological materials, including microorganisms. By combination with other pathogens, such as inter alia viruses, rickettsiae, bacteria, fungi and microsporidia, it is possible to bring about an advantageous increase in the action of the crystal toxin.

In a preferred embodiment of the invention, the proteins according to the invention are used together with spores of *Bacillus popilliae* and/or *Bacillus thuringiensis*. The spores of *Bacillus sphaericus* are also very suitable.

In another, likewise very advantageous variant, the proteins according to the invention are used in combination with cytolysing proteins and/or receptor proteins for the gut epithelium of scarabaeids, preferably in the form of fusion proteins.

In a further variant, the proteins according to the invention are used in combination with fungus spores.

It is also possible to use the protein(s) according to the invention, alone or in combination with at least one other substance, in the control of soil-borne organisms that damage plants and/or fungi and/or transmit diseases. The control includes the inactivation, especially the inhibition of the feeding activity, and/or the destruction of the soil-borne organisms in question.

For obtaining or producing the proteins according to the invention there is proposed a method in which one or more of the polynucleotides according to the invention is introduced (transformed) into a microorganism (e.g. a bacterium, virus, fungus or protozoon) or into a cell of an animal or plant cell culture, is subjected to the regulation and control of a promoter, preferably a regulatable promoter, naturally present in that microorganism or cell or present therein as a consequence of a/the recombination, and is expressed. In an especially preferred variant of the method, the polynucleotide(s) is(are) introduced into a bacterium of the *Bacillus thuringiensis* species.

The invention also includes the possibility of transferring polynucleotides according to the invention into plants or parts of plants in order to protect them from being eaten by scarabaeids. In other words: the invention includes also the use of polynucleotides according to the invention in the production of transgenic plants having the capacity to synthesise in all or some of the plant tissue a crystal protein that is identical or similar to the crystal protein characteristic of *Bacillus popilliae* and that is suitable for the inhibition of the feeding activity and/or for the destruction of larval and/or adult scarabaeids, especially Melolontha species and species closely related thereto, and/or in the inactivation and/or destruction of soil-borne organisms that damage plants and/or fungi and/or transmit diseases.

To that end, a method is proposed for the production of plants or plant tissue or plant propagation material with recombined genetic material that comprises a heterologous polynucleotide according to the invention, the expression of which results in a protein identical or similar to the crystal protein occurring naturally and characteristically in *Bacillus popilliae*. In the method according to the invention, plant cells or plant tissue are transformed with a recombinant DNA that comprises a polynucleotide according to the invention and, in addition, regulatory nucleotide sequences that are able to effect stable integration and expression of the polynucleotide in the plant cells; the plant or its propagation material, or both, is(are) then regenerated from the plant cells transformed with the heterologous DNA or from the corresponding tissue; and if desired the regenerated plant or its propagation material, or both, is(are) reproduced biologically.

The invention relates also to the genetically engineered transformed cells that have been produced using that method or another method, having stably integrated into their genome a (recombined) heterologous DNA comprising a polynucleotide according to the invention that encodes a protein identical or similar to the crystal protein occurring naturally and characteristically in *Bacillus popilliae*, the protein being expressed under the control of a promoter that is recognised by the polymerases of the cells and is naturally present in the cells or is present therein as a consequence of a/the recombination.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

A. Construction of a Nucleotide Sequence Encoding a *Bacillus popilliae* Crystal Protein

Example 1

Preparation of a Polynucleotide According to the Invention

A strain of *Bacillus popilliae* subsp. *melolonthae* is isolated from grubs of *Melolontha melolontha*. From the bacterial cells of that strain, firstly the total DNA material is prepared using current procedures and secondly the crystal protein is isolated and purified and its amino acid sequence is determined (in a commercially available protein sequenator). Oligonucleotides corresponding to partial sequences from the two end regions of the protein are synthesised for the purpose of acting as primers in a polymerase chain reaction (PCR) for the synthesis of a DNA probe for the crystal protein gene. The PCR is carried out using the total DNA from *Bacillus popilliae* subsp. *melolonthae*.

Alternatively, the isolated crystal protein can first be cleaved into short fragments, then the amino acid sequence of some of those fragments can be determined and, by comparison with the amino acid sequence of the Cry II A protein from *Bacillus thuringiensis* known in the prior art, two fragments can be selected that are presumed to originate from the two end regions of the protein. The DNA sequences corresponding to those fragments are then prepared as oligonucleotides and used as primers for the PCR synthesis. The PCR product is used as a probe for Southern Blot hybridisation. A 5.3 kB Eco RI fragment of the *Bacillus popillae* genome is identified by that procedure. The 5.3 kB Eco RI fragment is, for example, inserted into the plasmid pBCSK+ and cloned in the *E. coli* strain XL 1 Blue MRF'.

Sequencing of that 5.3 kB Eco RI fragment, for example by means of the Sanger chain reaction termination method, using commercially available sequenase test systems, e.g. a T7 Sequencing Kit, produces the result shown in the sequence listing SEQ ID NO:1.

Example 2

Genetically Engineered Production of a Crystal Protein According to the Invention The 5.3 kB Eco RI fragment of the *Bacillus popilliae* genome obtained according to Example 1 is inserted into a plasmid for gram-positive bacteria and introduced into bacterial cells of a crystal-free strain of *Bacillus thuringiensis* subsp. *kurstaki*. Especially suitable as plasmid is a plasmid known as a cloning vector for *Bacillus thuringiensis*, such as pHT304, pHT315 or pHT370, the production of which is described in the publication by O. Arantes and D. Lerecius in *Gene*, 148 (1991), pages 115–119. In that respect reference is made to that publication and the contents of that publication are herewith incorporated into the present description.

Recombined bacteria are replicated or cloned and, if necessary, stimulated to synthesise the crystal protein. This is effected by inducing spore formation, preferably simply by modifying the culture conditions in a selective manner.

The freeing of the protein is then induced by, for example, initiating spore germination or autolysis of the sporangia by making a further modification to the culture conditions. The freed protein is separated from the culture medium, purified and, if necessary, stored under cool, dry, dark conditions until used.

Example 3

Use of the Crystal Protein According to the Invention in the Control of Scarabaeids of the *Melolontha melolontha* Species.

1. Adult Scarabaeids

Adult may bugs (*Melolontha melolontha*) are kept in cages for 10 days under true-to-nature conditions. After 2 days, an aqueous suspension of the protein according to the invention is administered to 20 animals. The ingestion of food is immediately inhibited. After only 4 days, 12 animals (=60%) are dead. In practice, the preparation is sprayed onto the beetles' feed plants.

2. Scarabaeid Larvae (Grubs)

Grubs of the may bug (*Melolontha melolontha*) are dug up on open ground, kept individually in breeding vessels in the laboratory and fed on slices of carrot. After 3 weeks, the protein according to the invention in an aqueous suspension with or without spores is fed to 10 animals. As early as one day later, the ingestion of food is greatly reduced, inhibited. In practice, the preparation, possibly in combination with other pathogens and preferably together with bait, is incorporated into the soil.

B. Expression of the Nucleic Acid Sequences of the Invention in Heterologous Microbial Hosts Microorganisms which are suitable for the heterologous expression of the nucleotide sequences of the invention are all microorganisms which are capable of colonizing plants or the rhizosphere. As such they will be brought into contact with insect pests. These include gram-negative microorganisms such as Pseudomonas, Enterobacter and Serratia, the gram-positive microorganism Bacillus and the fungi Trichoderma, Gliocladium, and *Saccharomyces cerevisiae*. Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum, Gliocladium virens,* and *Saccharomyces cerevisiae*.

Example 4

Expression of the Nucleotide Sequences in *E. coli* and Other Gram-Negative Bacteria Many genes have been expressed in gram-negative bacteria in a heterologous manner. Expression vector pKK223-3 (Pharmacia catalogue #27-4935-01) allows expression in *E. coli*. This vector has a strong tac promoter (Brosius, J. et al., *Proc. Natl. Acad. Sci. U.S.A.* 81) regulated by the lac repressor and induced by IPTG. A number of other expression systems have been developed for use in *E. coli*. The thermoinducible expression vector $_pP_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, expression of the nucleotide sequence in closely related gram negative-bacteria such as Pseudomonas, Enterobacter, Serratia and Erwinia is possible. For example, pLRKD211 (Kaiser & Kroos, Proc. Natl. Acad. Sci. U.S.A. 81: 5816–5820 (1984)) contains the broad host range replicon ori T which allows replication in many gram-negative bacteria.

In *E coli*, induction by IPTG is required for expression of the tac (i.e. trp-lac) promoter. When this same promoter (e.g. on wide-host range plasmid pLRKD211) is introduced into Pseudomonas it is constitutively active without induction by IPTG. This trp-lac promoter can be placed in front of any gene or operon of interest for expression in Pseudomonas or any other closely related bacterium for the purposes of the constitutive expression of such a gene. Thus, a nucleotide sequence whose expression results in an insecticidal toxin can therefore be placed behind a strong constitutive promoter, transferred to a bacterium which has plant or rhizosphere colonizing properties turning this organism to an insecticidal agent. Other possible promoters can be used for the constitutive expression of the nucleotide sequence in gram-negative bacteria. These include, for example, the promoter from the Pseudomonas regulatory genes gafA and lemA (WO 94/01561) and the *Pseudomonas savastanoi* IAA operon promoter (Gaffney et al., *J. Bacteriol.* 172: 5593–5601 (1990).

Example 5

Expression of the Nucleotide Sequences in Gram-Positive Bacteria

Heterologous expression of the nucleotides sequence in gram-positive bacteria is another means of producing the insecticidal toxins. Expression systems for Bacillus and Streptomyces are the best characterized. The promoter for the erythromycin resistance gene (ermR) from *Streptococcus pneumoniae* has been shown to be active in gram-positive aerobes and anaerobes and also in *E. coli* (Trieu-Cuot et al., Nucl Acids Res 18: 3660 (1990)). A further antibiotic resistance promoter from the thiostreptone gene has been used in Streptomyces cloning vectors (Bibb, Mol Gen Genet 199: 26–36 (1985)). The shuttle vector pHT3101 is also appropriate for expression in Bacillus (Lereclus, FEMS Microbiol Lett 60: 211–218 (1989)). A significant advantage of this approach is that many gram-positive bacteria produce spores which can be used in formulations that produce insecticidal agents with a longer shelf life. Bacillus and Streptomyces species are aggressive colonizers of soils

Example 6

Expression of the Nucleotide Sequences in Fungi

*Trichoderma harzianum* and *Gliocladium virens* have been shown to provide varying levels of biocontrol in the field (U.S. Pat. No. 5,165,928 and U.S. Pat. No. 4,996,157, both to Cornell Research Foundation). A nucleotide sequence whose expression results in an insecticidal toxin could be expressed in such a fungus. This could be accomplished by a number of ways which are well known in the art. One is protoplast-mediated transformation of the fungus by PEG or electroporation-mediated techniques. Alternatively, particle bombardment can be used to transform protoplasts or other fungal cells with the ability to develop into regenerated mature structures. The vector pAN7-1, originally developed for Aspergillus transformation and now used widely for fungal transformation (Curragh et al., *Mycol. Res.* 97(3): 313–317 (1992); Tooley et al., *Curr. Genet.* 21: 55–60 (1992); Punt et al., Gene 56: 117–124 (1987)) is engineered to contain the nucleotide sequence. This plasmid contains the *E. coli* the hygromycin B resistance gene flanked by the *Aspergillus nidulans* gpd promoter and the trpC terminator (Punt et al., Gene 56: 117–124 (1987)).

C. Formulation of the Insecticidal Toxin

Insecticidal formulations are made using active ingredients which comprise either the isolated toxin or alternatively suspensions or concentrates of cells which produce it and which are described in the examples above. For example, Bt or *E. coli* cells expressing the insecticidal toxin may be used for the control of the insect pests. Formulations are made in liquid or solid form and are described below.

Example 7

Liquid Formulation of Insecticidal Compositions

In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethylene glycol ether (36 moles of ethylene oxide) | 5% | — | — |

-continued

| 1. Emulsifiable concentrates: | a | b | c |
|---|---|---|---|
| Tributylphenol polyethylene glyco ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–190°) | — | — | 94% | — |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgit | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 8

Solid Formulation of Insecticidal Compositions

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |

-continued

| 1. Wettable powders: | a | b | c |
|---|---|---|---|
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

The insecticidal formulations described above are applied to the plants according to methods well known in the art, in such amounts that the insect pests are controlled by the insecticidal toxin.

D. Expression of the Nucleotide Sequences in Transgenic Plants

The nucleic acid sequences described in this application can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgtl1, λgtl0 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the nucleotide sequence of the invention confer insect resistance to the transgenic plants.

Example 9

Modification of Coding Sequences and Adjacent Sequences

The nucleotide sequences described in this application can be modified for expression in transgenic plant hosts. A host plant expressing the nucleotide sequences and which produces the insecticidal toxins in its cells has enhanced resistance to insect attack and is thus better equipped to withstand crop losses associated with such attack.

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (Science 261: 754–756 (1993)) have expressed the Pseudomonas nahG gene in transgenic plants under the control of the CaMV 35S promoter and the CaMV tml terminator successfully without modification of the coding sequence and with x bp of the Pseudomonas gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C. and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (NAR 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | |
| --- | --- | --- | --- | --- | --- | --- | --- | --- | --- |
| -10 | -9 | -8 | -7 | -6 | -5 | -4 | -3 | -2 | -1 |
| C 3 | 8 | 4 | 6 | 2 | 5 | 6 | 0 | 10 | 7 |
| T 3 | 0 | 3 | 4 | 3 | 2 | 1 | 1 | 1 | 0 |
| A 2 | 3 | 1 | 4 | 3 | 2 | 3 | 7 | 2 | 3 |
| G 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Example 10

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and Arabidopsis—Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The Arabidopsis ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1:3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Inducible Expression, the PR-1 Promoter:

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6xGAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is described by de Framond (FEBS 290: 103–106 (1991)) and also in the published patent application EP 0 452 269, which is herein incorporated by reference. This promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunl gene. Xu et al. show that a wound-inducible promoter from the dicotyledon potato (pin2) is active in the monocotyledon rice. Further, Rohrmeier & Lehle describe the cloning of the maize Wipl cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. U.S.A. 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783

(1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 11

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below, the construction of two typical vectors suitable for Agrobacterium transformation is described.

a. pCIB200 and pCIB2001:

The binary vectors pcIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et al EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Example 12

Transformation

Once a nucleic acid sequence of the invention has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus Agrobacterium can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or micro-injection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using Agrobacterium has also been described. See, WO 94/00977 and U.S. Pat. No. 5,591,616, both of which are incorporated herein by reference.

3. Transformation of Plastids

Seeds of *Nicotiana tabacum* c.v. 'Xanthi nc' are germinated seven per plate in a 1' circular array on T agar medium and bombarded 12–14 days after sowing with 1 μm tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings are incubated on T medium for two days after which leaves are excised and placed abaxial side up in bright light (350–500 μmol photons/m$^2$/s) on plates of RMOP medium (Svab, Z., Hajdukiewicz, P. and Maliga, P. (1990) *PNAS* 87, 8526–8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) PNAS 91, 7301–7305) and transferred to the greenhouse.

E. Breeding and Seed Production

Example 13

Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); Crop Breeding, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 14

Seed Production

In seed production, germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods exemplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be designed for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a gene of the present invention that is expressed in said transformed plant at higher levels than in a wild type plant, together with a suitable carrier, together with label instructions for the use thereof for conferring broad spectrum disease resistance to plants.

The above disclosed embodiments are illustrative. This disclosure of the invention will place one skilled in the art in possession of many variations of the invention. All such obvious and foreseeable variations are intended to be encompassed by the appended claims.

What is claimed is:

1. An isolated nucleic acid molecule comprising a nucleotide sequence that encodes a protein having insecticidal activity against scarabaeids, said protein comprising an amino acid sequence that is the translation product of a nucleic acid sequence whose complement hybridizes to SEQ ID NO:1 under hybridization conditions of 7% sodium dodecyl sulfate (SDS), 0.5 M NaPO$_4$, 1 mM EDTA at 50° C. with washing in 0.1×SSC, 0.1% SDS at 50° C., or under hybridization conditions of 7% sodium dodecyl sulfate (SDS), 0.5 M NaPO$_4$, 1 mM EDTA at 50° C. with washing in 0.1×SSC, 0.1% SDS at 65° C.

2. An isolated nucleic acid molecule according to claim 1 wherein said nucleotide sequence comprises SEQ ID NO:1.

3. A chimeric nucleic acid molecule comprising a heterologous promotor sequence operatively linked to the nucleic acid molecule of claim 1.

4. A recombinant vector comprising the chimeric nucleic acid molecule of claim 3.

5. A transgenic host cell comprising the chimeric nucleic acid molecule of claim 3.

6. The transgenic host cell of claim 5, which is a transgenic plant cell.

7. A transgenic plant comprising the transgenic plant cell of claim 6.

8. Seed of the transgenic plant of claim 7.

9. A method of producing a transgenic plant resistant to scarabaceids, comprising introducing a chimeric nucleic acid molecule according to claim 3 into said plant, wherein said nucleic acid molecule is expressed in said plant in an effective amount to control scarahaeids.

10. An isolated nucleic acid molecule comprising a nucleotide sequence that encodes a protein having insecticidal activity against scarabaeids, wherein said nucleotide sequence has a complement that hybridizes to SEQ ID NO:1 under hybridization conditions of 7% sodium dodecyl sulfate (SDS), 0.5 M NaPO$_4$, 1 mM EDTA at 50° C. with washing in 0.1×SSC, 0.1% SDS at 50° C., or under hybridization conditions of 7% sodium dodecyl sulfate (SDS), 0.5 M NaPO$_4$, 1 mM EDTA at 50° C. with washing in 0.1×SSC, 0.1% SDS at 65° C.

11. A chimeric nucleic acid molecule comprising a heterologous promoter sequence operatively linked to the nucleic acid molecule of claim 10.

12. A recombinant vector comprising the chimeric nucleic acid molecule of claim 11.

13. A transgenic host cell comprising the chimeric nucleic acid molecule of claim 11.

14. The transgenic host cell of claim 13, which is a transgenic plant cell.

15. A transgenic plant comprising the transgenic plant cell of claim 14.

16. Seed of the transgenic plant of claim 15.

17. A method of producing a transgenic plant resistant to scarabaeids, comprising introducing a chimeric nucleic acid molecule according to claim 11 into said plant, wherein said nucleic acid molecule is expressed in said plant in an effective amount to control scarabaeids.

* * * * *